United States Patent [19]

Bortnick

[11] Patent Number: 4,546,493
[45] Date of Patent: Oct. 15, 1985

[54] TAN-THROUGH WEARING APPAREL AND PROCESS FOR MAKING THE SAME

[76] Inventor: Kenneth A. Bortnick, Rte. 2, Box 154, Parsonsburg, Md. 21849

[21] Appl. No.: 428,871

[22] Filed: Sep. 30, 1982

[51] Int. Cl.$^4$ .......................... A41D 7/00; A62B 17/00
[52] U.S. Cl. ................................. 2/67; 2/69; 2/243 R; 139/420 R; 427/407.1; 427/412; 428/229; 428/258
[58] Field of Search ........................ 2/67, 69, 2, 243 R; 139/420 R, 420 A, 420 C; 428/229, 258, 428, 446; 427/168, 407.1, 412

[56] References Cited

U.S. PATENT DOCUMENTS

| | | | |
|---|---|---|---|
| 2,391,959 | 1/1946 | Gallowhur | 2/67 X |
| 3,914,469 | 10/1975 | Delano et al. | 2/67 X |
| 4,066,106 | 1/1978 | Graham | 28/178 X |
| 4,115,615 | 9/1978 | Overstraeten | 2/67 X |
| 4,197,230 | 4/1980 | Baney et al. | 2/67 X |

Primary Examiner—H. Hampton Hunter
Attorney, Agent, or Firm—Shlesinger, Arkwright, Garvey & Fado

[57] ABSTRACT

A clothing apparel which is substantially transparent to ultra-violet light wavelengths; and, a coating applied to said fabric for preventing the transmission of light rays of a pre-determined wavelength through said fabric when said fabric is wet by water is disclosed.

13 Claims, 4 Drawing Figures

TAN-THROUGH WEARING APPAREL AND PROCESS FOR MAKING THE SAME

BACKGROUND OF THE INVENTION

The disclosed invention relates to garments, or wearing apparel, through which ultra-violet light rays may pass. The ultra-violet light rays, particularly those with a wave length of 320 to 400 nanometers, cause the skin of humans to become pigmentised or, as is commonly known, tanned.

Many people who choose to become tan choose to do so by lying in the sun on warm sunny days. If one should be located in the cooler parts of the country, then the number of days for lying in the sun is limited due to the weather. Consequently, a garment allowing one to tan while wearing the garment would increase the number of days during which one could acquire a tan.

Additionally, certain skin diseases, such as psoriasis, pityriasis, rosea, and vitiligo among others, may be partially alleviated by exposure to sun light. A component of sun light is light rays from the ultra-violet spectrum. Consequently, a fabric allowing the transmission of light rays from the ultra-violet spectrum through the threads of the fabric would aid in the treatment of these diseases.

OBJECTS OF THE INVENTION

The primary object of the disclosed invention is to provide wearing apparel which is composed of a fabric which is substantially transparent to light rays from the ultra-violet spectrum.

An additional object of the disclosed invention is to provide a coating on the fabric so that the coated fabric does not become transparent to all wavelengths of light when the coating and fabric become wetted by water.

Yet another object of the disclosed invention is to provide wearing apparel which is composed of a fabric which is substantially transparent to light rays having a wavelength less than 400 nanometers and visibly opaque to those above 400 nanometers.

Still another object of the disclosed invention is to provide a fabric which is durable and waterproof.

Yet a further object of the disclosed invention is to provide a fabric which may be used in the treatment of skin diseases for which exposure to ultra-violet wavelengths is beneficial.

These and other objects and advantages of the invention will be readily apparent if view of the following description and drawings of the above described invention.

DESCRIPTION OF THE DRAWINGS

The above and other objects and advantages and novel features of the present invention will become apparent from the following detailed description of the preferred embodiment of the invention illustrated in the accompanied drawings, wherein:

Referring now to FIG. 1, the fabric F is composed of weft threads 10 and warp threads 12 which may be woven by any acceptable method.

Figure 1:
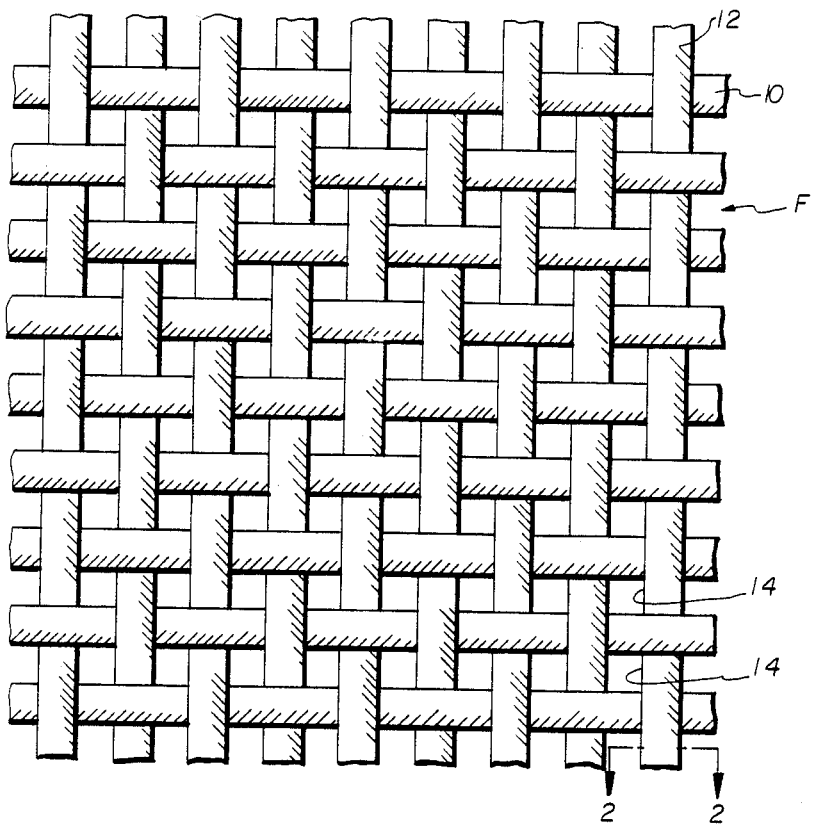
FIG. 1 is a top plan view of the fabric of the invention disclosing the threads of which the fabric is composed.

The threads, 10 and 12, are composed of a material which is substantially transparent to light rays from the ultra-violet spectrum. More particularly, the threads, 10 and 12, allow light rays with a wavelength below 400 nanometers to pass virtually unreflected through the threads.

The material of which the threads, 10 or 12, is composed is approximately 99.5% by weight, or greater, silicon dioxide, $SiO_2$. Materials with an $SiO_2$ content less than 99.5% by weight will permit some transmission of ultra-violet but the amount transmitted decreases significantly as the $SiO_2$ content decreases.

Threads or woven fabric containing the appropriate percentage of $SiO_2$ may be purchased from the J. P. Stevens Company under the trade name Astroquartz or from Alpha Associates Company under the trade name Alphaquartz. Preferably, the woven fabric has a thickness of between 0.009 to 0.011 inches.

The $SiO_2$ fabric from J. P. Stevens Company comes with a binder applied to the fabric to help retain a coating on the fabric threads. The binder typically used is designated A 1100 by J. P. Stevens. Binders A 172, S 22-60 and Z 60-30 may also be used, if desired. The use of a binder is not necessary in carrying out this present invention.

The $SiO_2$ fabric, even when coated with the binder, frays easily and becomes substantially transparent to all wavelengths of light when wetted by water. Consequently, a coating on the threads is necessary in order to improve the durability of the fabric and to prevent the fabric from becoming transparent to all wavelengths when the fabric is wet. The coating must also be substantially transparent to light rays from the ultra-violet spectrum.

The coating employed is a silicone-based compound which has been sufficiently thinned so that it may be applied to the fabric threads. Silicone is a generic term used to describe a family of polymers that possess polysiloxane backbones. Side groupings added to the polysiloxane backbones determine the properties of the final product.

Acceptable examples of suitable silicone compounds are; Laur's 101 CBA silicon-rubber dispersion as manufactured by Laur Silicone Rubber Compounding, Inc.; Dow Corning 100% Silicone rubber general purpose sealant and, General Electric's Clear Glue and Sealant.

Acceptable thinning components would include, but not be limited, to heptane, designated by the chemical formula $C_7H_{16}$, and methyl ethyl ketone, designated chemically as $CH_3COCH_2CH_3$. Although heptane and methyle ethyl ketone are disclosed, any number of suitable thinning compounds may be employed and the invention is not restricted to the thinning components recited.

The fabric, prior to being coated with the coating compound, is slightly translucent and has a milky white color due to the number of threads. The uncoated fabric, when wet with water, becomes transparent to substantially all wavelengths of light. Consequently, such a fabric is unsuitable for bathing suits or other garments where such a transparent garment would be inappropriate.

The coating, and consequently the fabric of the invention, may be colored with a dye compound which permits the transmission of portion of the light from the ultra-violet spectrum. An acceptable dye is Tricon Colors Inc., Oil Blue 15134 heptane soluable dye. The invention is not limited to this dye any ultra-violet transmitting dye is acceptable. Nor is the invention limited to blue dye.

After being coated with the above described coating compound, the fabric remains slightly translucent and has an off-white color. The fabric is much more durable but not as flexible as the untreated fabric.

The coating compound may be sprayed onto the fabric, after the threads have been woven into a fabric, when the silicone compound has been sufficiently thinned. Likewise, the fabric may be dipped into the coating compound after the garments have been manufactured.

Yet another way of manufacturing the fabric of the invention is to individually coat the threads prior to their being woven into a fabric. In this way, the apertures 14 between the threads, 10 and 12, will not become clogged with the coating compound and the fabric will, therefore, more readily permit the passage of air through the fabric or as is commonly known, breathe.

In an additional embodiment of the disclosed invention one of the threads, 10 or 12, may be made of a material other than SiO2. For example, cotton threads may be used so that the garment will be able to "breathe". Additionally, nylon, wool, polyester, or any other suitable material may be used. In order to use these additional thread materials it is desirable that the SiO2 threads be coated with the silicone-based coating compound prior to the weaving of the fabric.

Figure 2:
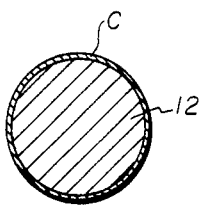
FIG. 2 is a cross-sectional view through a thread of the fabric.

Referring now to FIG. 2, the coating compound C surrounds the warp thread 12. The thickness of the compound C may be varied as necessary, but a coating of 0.0005 to 0.001 inches is preferable. It is necessary that the dried coating compound C be thick enough to prevent the fabric F from becoming substantially transparent to all wavelengths of light when the fabric becomes wet by water. By preventing the fabric from becoming substantially transparent to all wavelengths, the garment may be worn at all times, even while wet.

Figure 3:
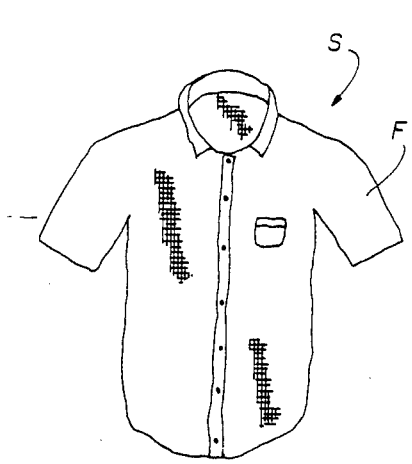
FIG. 3 is a shirt manufactured from the fabric of the invention.

FIG. 3 illustrates the use of a fabric F in the manufacturing of a shirt S.

Figure 4:
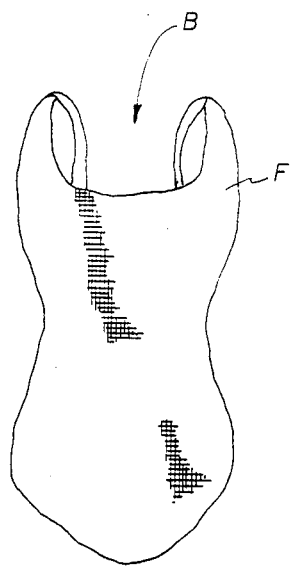
FIG. 4 is a swim suit manufactured from the fabric of the invention.

FIG. 4 illustrates the use of fabric F in the manufacture of a bathing suit B.

While this invention has been described as having a preferred form, it is understood that it is capable of further modifications, uses and/or adaptations of the invention following in general the principal of the invention and including such departures from the present disclosure as come within known or customary practice in the art to which the invention pertains, as may be applied to the central features hereinbefore set forth, and fall within the scope of the invention of the limits of the appended claims.

What I claim:

1. Tan-through wearing apparel, comprising:
   a. a fabric composed of a material which is substantially transparent to ultra-violet wavelengths and to substantially all wavelengths of light when wet; and,
   b. a coating on said fabric for preventing the transmission of light rays of a pre-determined wavelength through said fabric when said apparel is wet.

2. Tan-through wearing apparel as defined in claim 1, wherein:
   a. said fabric is composed of a number of weft threads and warp threads; and,
   b. said threads comprised in part of silicon dioxide.

3. Tan-through wearing apparel as defined in claim 1, wherein:
   a. said coated fabric is cut and sewn into the general shape and form of wearing apparel.

4. Tan-through wearing apparel as defined in claim 1, wherein:
   a. said coating is comprised substantially of a silicone base compound.

5. Tan-through wearing apparel as defined in claim 2, wherein:
   a. at least some of said threads are composed of cotton.

6. Tan-through wearing apparel, comprising:
   a. a fabric composed of a material which is at least 99.5% by weight silicon dioxide; and,
   b. a coating comprised essentially of a silicone based compound which is adapted for substantially preventing the transmission of light of wavelength in excess of 400 nanometers through said fabric when said apparel is wet.

7. Tan-through wearing apparel as defined in claim 1, wherein:
   a. said compound prevents the transmission of light rays with a wavelength in excess of 400 nanometers through said fabric when said apparel is wet.

8. A process for creating tan-through wearing apparel, comprising the steps of:
   a. weaving a fabric with warp threads and weft threads composed of a material substantially transparent to ultra-violet wavelengths; and,
   b. coating said fabric with a compound having the characteristic of preventing the transmission of light rays of a pre-selected wavelength through said fabric when said coated fabric is wet by water.

9. A process for creating tan-through wearing apparel as defined in claim 8, wherein:
   a. coating of said threads with said coating compound occurs prior to said threads being woven into said fabric.

10. A process for creating tan-through wearing apparel a defined in claim 8, wherein:
    a. coating of said threads with said coating compound occurs after said fabric has been woven.

11. A process for creating tan-through apparel, comprising the steps of:
    a. coating a first thread composed of a material substantially transparent to ultra-violet wavelengths with a compound adapted for preventing the transmission of light rays of a pre-selected wave through said thread when said coated thread is wet;
    b. weaving said coated thread and a second thread into a fabric.

12. Tan-through wearing apparel as defined in claim 1, further comprising:
    a. an ultra-violet transmitting dye is added to said coating compound for coloring said compound.

13. Tan-through wearing apparel, comprising:
    a. a material transparent at all times to sun light, including ultra-violet radiation;
    b. said material not incorporating therein sun screening materials; and,
    c. a translucent coating applied to said material and having the characteristic of filtering out selected wavelengths of light, said coating having the additional characteristic of being translucent under wet and dry conditions.

* * * * *